United States Patent [19]
Fleury

[11] Patent Number: 5,979,223
[45] Date of Patent: Nov. 9, 1999

[54] DEVICE INTENDED FOR MEASUREMENTS ON A POROUS SAMPLE IN THE PRESENCE OF FLUIDS, USING TEMPERATURE-RESISTANT SEMIPERMEABLE MEMBRANES

[75] Inventor: Marc Fleury, La Celle Saint Cloud, France

[73] Assignee: Institut Francais du Petrole, Cedex, France

[21] Appl. No.: 09/066,936

[22] Filed: Apr. 28, 1998

[30] Foreign Application Priority Data

Apr. 29, 1997 [FR] France ................................. 97 05442

[51] Int. Cl.$^6$ ................................................. G01N 15/08
[52] U.S. Cl. ........................................................ 73/38
[58] Field of Search ............................................ 23/38

[56] References Cited

U.S. PATENT DOCUMENTS

| | | | |
|---|---|---|---|
| 2,345,935 | 4/1944 | Hassler | 73/38 |
| 2,465,948 | 3/1949 | Welge | 73/38 |
| 2,534,737 | 12/1950 | Rose | 73/38 |
| 2,612,036 | 9/1952 | Angona | 73/38 |
| 2,745,057 | 5/1956 | Dotson | 73/38 |
| 4,561,289 | 12/1985 | Jones . | |
| 4,857,080 | 8/1989 | Baker . | |
| 5,065,421 | 11/1991 | Morineau et al. | 73/38 X |
| 5,637,796 | 6/1997 | Deruyter et al. | 73/38 X |
| 5,679,885 | 10/1997 | Lenormand et al. | 73/38 |
| 5,698,772 | 12/1997 | Deruyter et al. | 73/38 |

FOREIGN PATENT DOCUMENTS

| | | | |
|---|---|---|---|
| 0371877 | 6/1990 | European Pat. Off. | 73/38 |
| 0729022 | 8/1996 | European Pat. Off. | 73/38 |

*Primary Examiner*—Daniel S. Larkin
*Attorney, Agent, or Firm*—Antonelli, Terry, Stout & Kraus

[57] ABSTRACT

Device intended for measurements on a porous rock bar in the presence of fluids including a containment cell comprising an elongate body (2) closed at the opposite ends thereof by end pieces (6, 7) and sources of pressurized fluids allowing displacement under pressure, within the sample, of a first wetting fluid and of a second fluid. One or more selectively wettable rigid membranes consisting each of a relatively thin layer of a porous ceramic on a support layer made from a porous material are pressed against the ends of the sample. The membranes can for example be made by sintering of metallic grains of unequal size (the grains are much coarser for the support layer). Such membranes have good resistance to high temperatures of the order of several hundred °C. Electrodes (E1) connected to a measuring device (24) are used to determine physical characteristics of the bar. The device can be used for oil reservoir engineering notably.

10 Claims, 3 Drawing Sheets

DEVICE INTENDED FOR MEASUREMENTS ON A POROUS SAMPLE IN THE PRESENCE OF FLUIDS, USING TEMPERATURE-RESISTANT SEMIPERMEABLE MEMBRANES

FIELD OF THE INVENTION

The present application relates to a device intended for measurements on a porous sample in the presence of fluids, using semipermeable membranes withstanding high temperatures, in order to determine some of the physical characteristics thereof.

Such a cell is for example well suited for testing geologic samples and for determining various parameters such as the capillary pressure of the rocks in drainage or imbibition phases, their wettability index, their relative permeability, their resistivity index, etc. Such a cell finds applications notably in the petroleum domain for testing reservoir rocks when enhanced recovery operations are for example carried out in a reservoir.

BACKGROUND OF THE INVENTION

In order to determine the wettability of rocks with respect to the water and the oil which may be contained therein, the initially water-saturated rock is, for example, subjected to a drainage process in order to decrease the saturation (Sw) thereof, then to an imbibition process allowing the water saturation thereof to be increased again. The capillary pressure at one point is defined as the difference Pc at equilibrium between the pressure Po of the oil and the pressure Pw of the water. This parameter makes sense only if the two fluids are in the continuous phase in the porous medium. For a water wet medium, only positive values make sense. On the other hand, if the medium has a mixed wettability, the fluids can remain in the continuous phase for the positive and for the negative capillary pressures (Pc) as well.

For an application of this type, a complete capillary pressure measuring cycle must therefore comprise (FIG. 4):

a) positive primary drainage of an initially 100% water-saturated sample (curve C1);

b) positive imbibition (curve C2);

c) negative imbibition (curve C3);

d) negative drainage (curve C4); and e) positive secondary drainage (curve C5).

Curves C2' and C3', respectively, correspond to a spontaneous imbibition and a negative primary imbibition.

Patent application EP-A-0,701,120 filed by the claimant describes a device intended for wettability measurements on porous rock samples in a containment cell delimited at the two opposite ends thereof by two end pieces. Channels run through these end pieces and communicate the grooved internal faces thereof respectively with two adjustable pressure fluid sources delivering, respectively, a first and a second fluid. The bar is placed in the cell within an elongate deformable sheath associated with pressure means intended to laterally exert a confining pressure, thereon. Two semipermeable membranes, respectively, permeable to the first and to the second fluid are placed between the internal faces of the end pieces and the sample. Wraparound electrodes are placed in the sheath, in contact with the lateral wall of the sample, on either side thereof. They are connected to a device measuring the electrical conductivity of the sample. The bar is at first initially saturated with a first fluid, such as brine, prior to being placed in the cell. A second fluid, oil for example, is injected under pressure at one end of the cell. It displaces the first fluid in the sample and the volume ejected is recovered at the opposite end. One or more of the next phases of the aforementioned measuring cycle are carried out thereafter.

A measuring device comprising means for measuring the electrical conductivity and the volume of the fluid ejected is placed in the cell, thus allowing to determine various physical parameters of the bar.

In a structure of this type, it is well-known to use as an oil wet membrane, a membrane for example made of Gore-Tex (registered trademark) which withstands the temperature range (up to 100 or 200° C.) observed during porous sample tests.

A thin plate made of porous ceramic, which fills its role as long as the operating temperature of the cell is not too high (preferably below 100° C.), is generally used as a water wet membrane. It is possible to use a ceramic membrane that is a few mm thick and which withstands the temperature better, but the drawback of such a membrane is that it notably slows the progress of the cycle of operations down.

SUMMARY OF THE INVENTION

The present invention relates to a device intended for measurements, in the presence of fluids, on a porous sample wettable by at least a first fluid and laterally confined by a deformable sheath, in order to determine physical characteristics of the sample, which allows to overcome the aforementioned drawbacks.

It comprises a cell including an elongate body closed at the opposite ends thereof by end pieces, pressure means for exerting a radial confining pressure on the sheathed sample, pumping means for communicating with the inside of the cell through the end pieces, in order to displace the first wetting fluid and at least a second fluid, and measuring means.

The device is characterized in that it comprises a two-layer membrane permeable to the first fluid, consisting of a support disk made from a porous material coated with a relatively thin porous ceramic layer (made for example by sintering of metallic grains), this two-layer membrane being placed in the cell in contact with a first end of the sample.

According to a preferred embodiment, the support disk is made of sintered metal obtained with coarser grains than those used for the thin layer.

A membrane comprising a thin layer of sintered alumina with 0.1 $\mu$m diameter metallic grains is for example produced, the support disk being made from sintered alumina with grains about 100 times as coarse as those used for the thin layer.

The two-layer membrane is preferably provided with a sealed peripheral coating made for example from nonporous ceramic, so as to prevent flows likely to bypass the membrane.

The device can also comprise another membrane wettable by the second fluid, placed in contact with the opposite end of the sample, which can be achieved by subjecting a two-layer membrane similar to the previous one to a chemical treatment which makes it wettable by the second fluid.

With such a two-layer membrane wettable by a first fluid, such as water or brine, and possibly another membrane of the same type made wettable by another fluid, capable of withstanding relatively high temperatures, a testing device can be obtained notably for testing geologic samples under temperature and pressure conditions reproducing those which can be found in situ in a reservoir for example, without the progress of the measuring cycles being hindered by the limitations specific to the membranes conventionally used.

BRIEF DESCRIPTION OF THE DRAWINGS

Other features and advantages of the device according to the invention will be clear from reading the description hereafter of a non limitative embodiment example, with reference to the accompanying drawings wherein.

DESCRIPTION OF THE PREFERRED EMBODIMENTS

Figure 1:
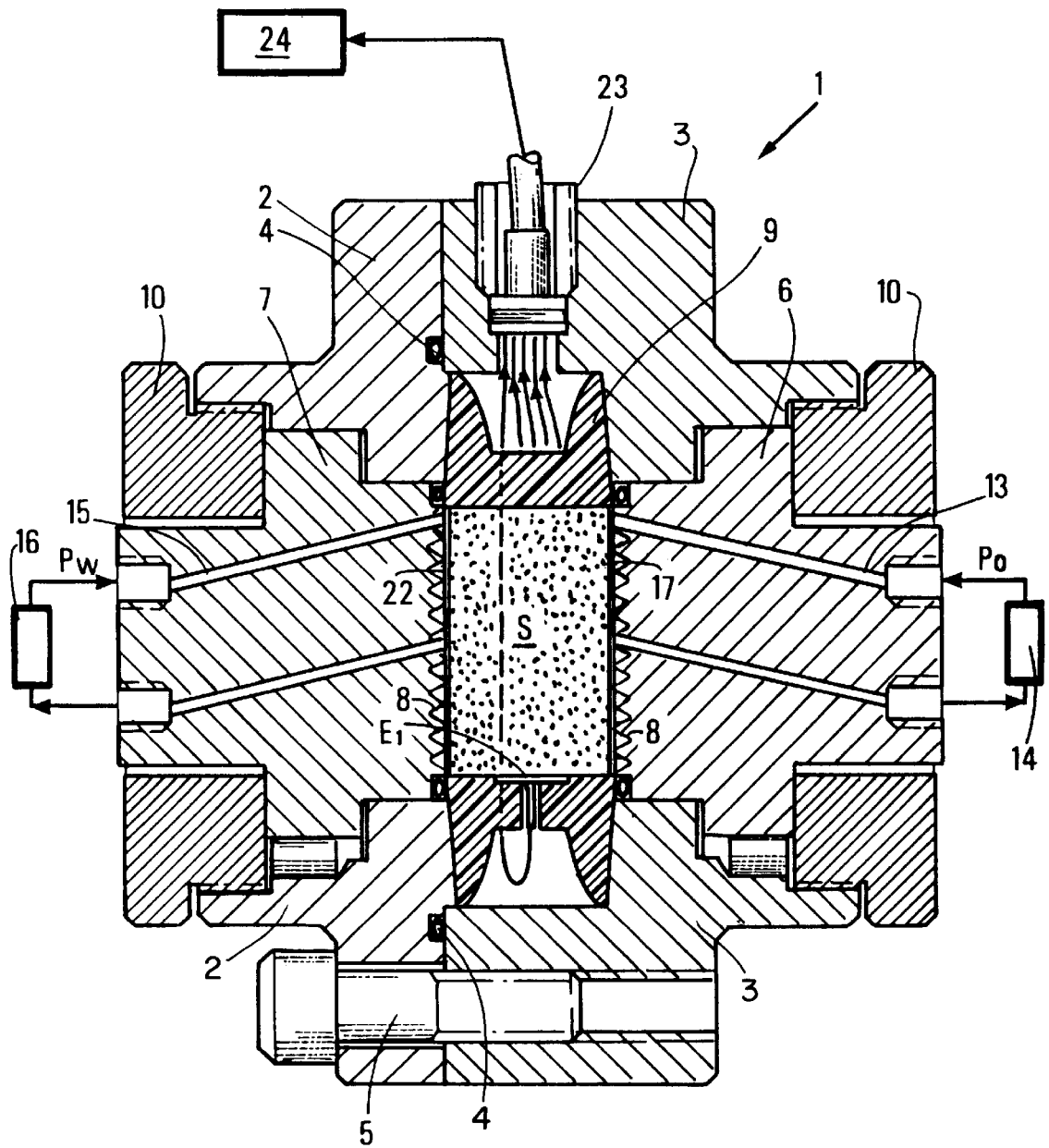
FIG. 1 diagrammatically shows an embodiment of the device in lengthwise section, FIG. 2 diagrammatically shows an example of a water wet two-layer membrane.
Figure 4:
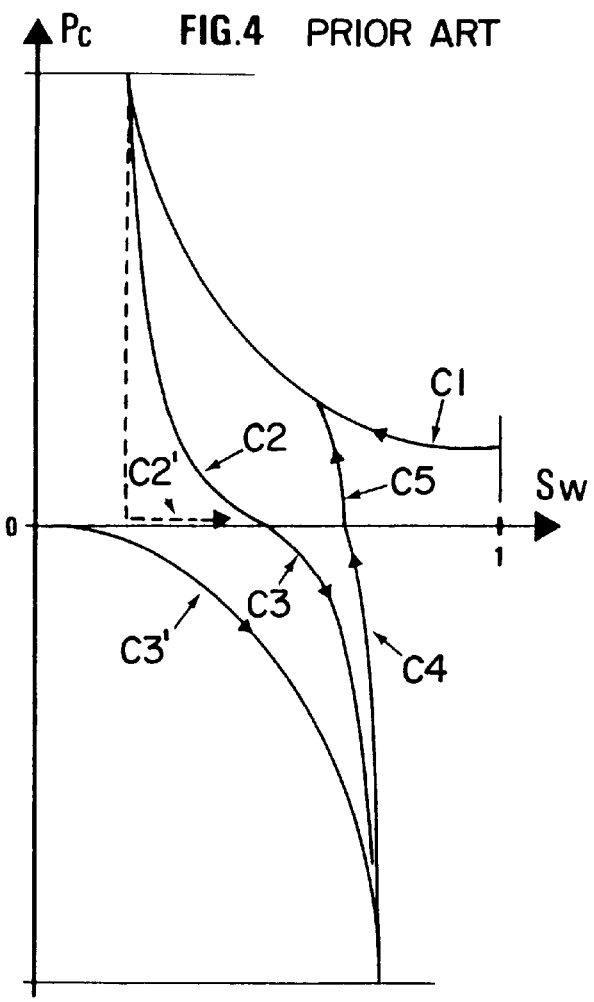
FIG. 4 shows, by way of example, the variations undergone by the capillary pressure in a sample during a complete drainage-imbibition cycle.
Figure 3:
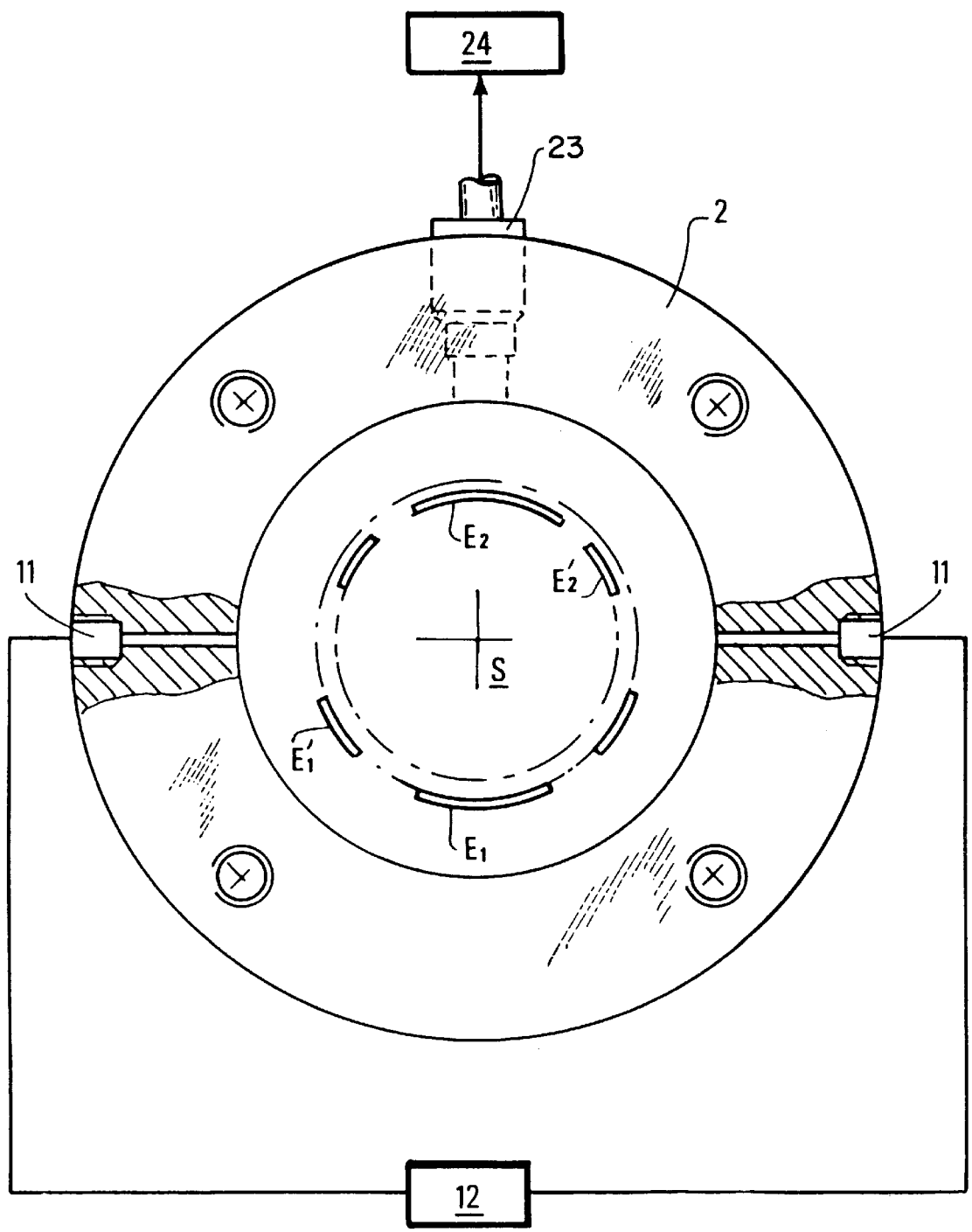
FIG. 3 shows a cross-sectional view of the latter embodiment.

According to the embodiment of FIG. 1, the device comprises a hollow body 1 consisting of two cylindrically symmetric sleeves 2, 3. They are pressed against each other by means of seals 4 and fixed together with screws 5. Each sleeve comprises an axial cavity for an end piece 6, 7 whose faces opposite each other are provided with spider-shaped grooves 8. Sample S is placed in an annular elastomer part forming sheath 9. The assembly made up of sample S and of sheath 9 is installed in an inner cavity of sleeve 3. Both end pieces 6, 7 are pressed against the sample by screwing two nuts 10 in sleeves 2, 3. Two radial openings 11 (FIG. 3) provided through the external wall of sleeve 2 allow an axial confining pressure to be applied by means of a pressure source 12.

Channels 13 run through end piece 6 and communicate the network of grooves 8, on the terminal face thereof, with a first source 14 delivering the first pressurized fluid. Similarly, channels 15 run through end piece 7 and communicate the corresponding network of grooves 8 with a second source 16 delivering the second pressurized fluid.

Figure 2:
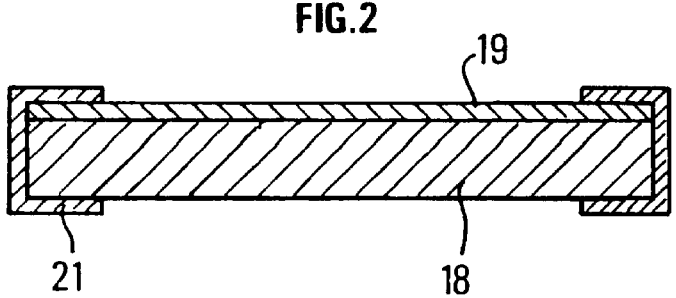

A first semipermeable membrane 17 permeable to a first fluid (brine as it is found in geologic samples for example) is pressed against the face of one end piece. This membrane comprises (FIG. 2) a first layer 18 permeable to water and acts as a support for a thin layer 19 made of porous ceramic. It is obtained for example by sintering of metallic grains. Sintered alumina can notably be used.

A thin 50-$\mu$m thick layer obtained through sintering from 0.1-$\mu$m diameter metallic grains is for example suited for pressures of the order of a few tenths MPa.

Metallic sinter made from coarser metallic grains can also be used as a support layer 18. A layer having a thickness of several millimeters (7 mm for example), made by sintering of grains having a diameter of several $\mu$m (10 $\mu$m for example), is typically used.

Such a two-layer membrane made from sintered material has the advantage of withstanding very well relatively high temperatures reproducing those (of the order of several hundred °C.) which rocks are subjected to in underground reservoirs.

In order to prevent bypass fluid leakage, a sealed annular coating 21 extending over the two opposite faces is formed around the membrane. This coating is for example made from nonporous ceramic (enamel).

Another semipermeable membrane 22 permeable to a second fluid such as oil is pressed against the other face. A microporous wall of a well-known type manufactured for example by Gore-Tex, Sartorius, Poretics, Millipore, etc., can be used.

According to an advantageous embodiment, membrane 22 wettable by the second fluid can also be a two-layer membrane similar to the membrane described above, which has been previously subjected to a suitable chemical treatment. For example, a treatment using a silanization reaction (based on organochlorosilane solutions) makes the porous ceramic highly oil wet. The substance called Quilon (registered trademark), which is a chromium complex having a hydrophobic acid group, can be used to modify the wettability.

The device comprises for example at least a first pair of electrodes E1, E2 (FIG. 3) placed in annular part 9, allowing an electric current to be applied, and at least a second pair of electrodes E'1, E'2 between which the potential difference created in response to the application of the electric current is measured. This separate assignment of the pairs of electrodes, one to the application of a current, the other to the measurement of potential differences, allows to prevent contact resistances.

Through a plug 23 provided with a bushing, the wires connected to the various electrodes are connected to an electrical conductivity measuring device 24 of a well-known type.

The device can be placed in a thermostat-controlled enclosure (not shown) designed to reproduce the temperature of the geologic formation from which the sample has been extracted.

I claim:

1. A device intended for measurements, in the presence of liquids, on a porous sample wettable by at least a first liquid in order to determine physical characteristics of the sample, comprising a cell including an elongate body closed at the opposite ends thereof by end pieces, a deformable sheath provided in the elongate body for laterally confining the sample, pressure means for exerting a radial confined pressure on the sheathed sample, pumping means communicating with the inside of the cell through said end pieces in order to displace the first wetting liquid and at least a second liquid, measuring means, a two-layer membrane wettable by said first liquid, consisting of a support disk made from a sintered porous material coated with a relatively thin layer made of a sintered porous material whose grains are much finer so that the permeability of two-layer membrane is substantially that of the thin layer, the two-layer membrane being placed in the cell in contact with a first end of sample.

2. A device as claimed in claim 1, characterized in that the ratio of the size of the grains used to form the support layer to that of the grains used to form the thin layer is at least 50.

3. A device as claimed in claim 2, characterized in that said size ratio is selected equal to 100.

4. A device as claimed in claim 1, characterized in that the support disk and the thin layer are made by sintering of metallic grains.

5. A device as claimed in claim 1, characterized in that said two-layer membrane permeable to the first liquid comprises a thin layer made from sintered alumina with grains having a diameter of the order of 0.1 $\mu$m, support disk being made from sintered alumina with grains about 100 times as coarse.

6. A device as claimed in claim 1, characterized in that the two-layer membrane is provided with a sealed peripheral coating (21) in order to prevent flows likely to bypass the membrane.

7. A device as claimed in claim 6, characterized in that the sealed peripheral coating is made of nonporous ceramic.

8. A device as claimed in claim 1, further comprising a second two-layer membrane wettable by the second liquid, placed in contact with the end of sample opposite said first end.

9. A device as claimed in claim 8, characterized in that said second two-layer membrane also comprises a superposition of two layers made by sintering of metallic powder, which have been subjected to a chemical treatment in order to make the second two-layer membrane wettable by said second liquid.

10. A device as claimed in claim 1, further comprising electrodes placed around the sample and connected to a device intended to measure the resistivity of the sample.

\* \* \* \* \*